United States Patent
Khatri

(10) Patent No.: US 9,446,166 B2
(45) Date of Patent: Sep. 20, 2016

(54) FIBRIN SEALANT COMPOSITIONS WITH CHEMICAL CROSSLINKING

(71) Applicant: ETHICON, INC., Somerville, NJ (US)

(72) Inventor: Chetan Anirudh Khatri, Acton, MA (US)

(73) Assignee: Ethicon, Inc., Somerville, NJ (US)

( * ) Notice: Subject to any disclaimer, the term of this patent is extended or adjusted under 35 U.S.C. 154(b) by 592 days.

(21) Appl. No.: 13/748,678

(22) Filed: Jan. 24, 2013

(65) Prior Publication Data

US 2014/0205636 A1 Jul. 24, 2014

(51) Int. Cl.
*A61K 31/74* (2006.01)
*A61L 24/00* (2006.01)

(52) U.S. Cl.
CPC .................................. *A61L 24/0094* (2013.01)

(58) Field of Classification Search
CPC .... A61K 9/08; A61K 9/0019; A61K 9/0021; A61L 26/0042; A61L 26/0033; A61L 26/0023; A61L 26/008
USPC .............. 424/444, 77, 78.06; 514/13.5, 13.7, 514/802, 800, 801
See application file for complete search history.

(56) References Cited

U.S. PATENT DOCUMENTS

| | | | |
|---|---|---|---|
| 5,137,875 A * | 8/1992 | Tsunenaga | A61L 27/20 514/17.2 |
| 6,096,309 A | 8/2000 | Prior | |
| 6,132,759 A | 10/2000 | Schacht | |
| 6,371,975 B2 | 4/2002 | Cruise | |
| 6,730,299 B1 | 5/2004 | Tayot | |
| 6,833,408 B2 | 12/2004 | Sehl | |
| 7,868,123 B2 | 1/2011 | Khatri | |
| 2003/0232746 A1 | 12/2003 | Lamberti | |
| 2005/0002893 A1 | 1/2005 | Goldmann | |
| 2006/0078536 A1* | 4/2006 | Kodokian | A61K 31/785 424/78.27 |
| 2007/0280988 A1 | 12/2007 | Ludwig | |
| 2008/0075657 A1 | 3/2008 | Abrahams | |
| 2008/0213243 A1 | 9/2008 | Preiss-Bloom | |
| 2008/0220047 A1 | 9/2008 | Sawhney | |
| 2008/0319101 A1 | 12/2008 | Nakajima | |

(Continued)

FOREIGN PATENT DOCUMENTS

| | | |
|---|---|---|
| EP | 308330 | 3/1989 |
| EP | 2100628 | 9/2009 |

(Continued)

OTHER PUBLICATIONS

Furlan et al., "Cross-Linking of Human Fibrinogen With Glutaraldehyde and Tetranitromethane", Thrombosis Research, vol. 7, pp. 827-838, 1975, Pergamon Press, Inc.

(Continued)

*Primary Examiner* — Micah-Paul Young
(74) *Attorney, Agent, or Firm* — David R. Crichton; Leo B. Kriksunov

(57) ABSTRACT

The invention relates to tissue adhesives or sealants, more specifically to fibrinogen based sealants reinforced with particulate material and chemically cross-linked. More particularly, the present invention is directed to tissue sealant, adhesive, hemostat, or scaffolding material containing thrombin, fibrinogen, a biocompatible particulate material having amine functionality, and a biocompatible polymer containing aldehyde groups. The present invention is also directed to methods for the use of such materials.

6 Claims, 2 Drawing Sheets

(56) References Cited

U.S. PATENT DOCUMENTS

| | | |
|---|---|---|
| 2009/0004239 A1* | 1/2009 | Ladet .................... A61F 2/02 424/423 |
| 2009/0010982 A1 | 1/2009 | Abrahams |
| 2009/0232877 A1* | 9/2009 | Montes .................. A61K 31/74 424/447 |
| 2010/0063459 A1 | 3/2010 | Preiss-Bloom |
| 2010/0166834 A1* | 7/2010 | Dockal et al. ................ 424/443 |
| 2010/0173843 A1 | 7/2010 | Hnojewyj |

FOREIGN PATENT DOCUMENTS

| | | |
|---|---|---|
| WO | WO 9422503 | 10/1994 |
| WO | WO 9800161 | 1/1998 |
| WO | WO 9966964 | 12/1999 |
| WO | WO 2008005207 | 1/2008 |

OTHER PUBLICATIONS

Ahmed et al., "Fibrin: A Versatile Scaffold for Tissue Engineering Applications", Tissue Engineering, Part B, vol. 14, No. 2, 2008, pp. 199-215.

Falstrom et al., "Reduction of Femoral Artery Bleeding Post Catheterization Using a Collagen Enhanced Fibrin Sealant", Catheterization and Cardiovascular Dioagnosis, 41:79-84, 1997.

Mackie et al., "Guidelines on fibrinogen assays", British Journal of Haematology, 2003, 121, 396-404.

* cited by examiner

FIBRIN SEALANT COMPOSITIONS WITH CHEMICAL CROSSLINKING

FIELD OF THE INVENTION

The invention relates to tissue adhesives or sealants, more specifically to fibrinogen based sealants reinforced with particulate material and chemically cross-linked.

BACKGROUND OF THE INVENTION

Biologic sealants comprising fibrinogen and thrombin are known. Cross-linked fibrin sealant is formed when fibrinogen and thrombin are mixed together but the formed fibrin sealant is subject to undergo enzymatic degradation with plasmin. Such sealants degrade and absorb in about 4 to 7 days, while the sealant mechanical strength and tissue bonding ability must be retained until the wound heals, which can take up to about 14 days. One method for controlling fibrin sealant enzymatic degradation has been to incorporate tranexamic acid or aprotinin into the tissue sealant formulation components. Other means have been explored for improving the strength of fibrin-based adhesive/sealants, such as incorporating collagen.

Fibrin hydrogels fall within a class of biomaterials that have great scaffolding potential in many tissue engineering applications due to their high tissue-like water content, high biocompatibility in general, mechanical properties that parallel the properties of soft tissues, efficient transport of nutrients and waste, powerful ability to uniformly encapsulate cells, and ability to be injected as a liquid that gels in situ. The fibrin hydrogel as a potential scaffold has low mechanical stiffness and rapid degradation before the proper formation of tissue engineered structures.

In order to improve the low mechanical stiffness for some tissue engineering applications, fibrin hydrogels can be combined with other scaffold materials such as gelatin, hyaluronic acid, chondroitin-6-sulfate, collagen and chitosan to obtain constructs with desired mechanical strength. To prolong degradation of fibrin glue several approaches have been taken, including introducing highly crosslinked Fibrin Micro Beads (FMBs) or removal of proteins that are believed to aid in degradation of fibrin clot for e.g. plasmin.

Published PCT Publication WO1999/066964 by Tammishetti et al. entitled "Carbodiimide crosslinked albumin for bioadhesives, surgical sealants, and implantable devices", teaches a method for producing a cross-linked albumin composition for use in a bioadhesive, surgical sealant or implantable device, comprising the steps of: (a) providing an albumin preparation; (b) providing a carbodiimide preparation; and (c) mixing said albumin preparation and said carbodiimide preparation under conditions which permit cross-linking of said albumin.

U.S. Pat. No. 6,371,975 by Cruise et al. entitled "Compositions, systems, and methods for creating in situ, chemically cross-linked, mechanical barriers" discloses a biocompatible and biodegradable barrier material that can be applied to a tissue region, e.g., to seal a vascular puncture site. The barrier material comprises a compound, which is chemically cross-linked without use of an enzyme to form a non-liquid mechanical matrix. The compound preferably includes a protein comprising recombinant or natural serum albumin that is mixed with a polyethylene glycol (PEG)-derived polymer, and, most preferably, a multi-armed PEG polymer.

U.S. Pat. No. 6,833,408 by Sehl, et al. teaches a method of repairing damaged tissue in a patient comprising the steps of: placing into contact with the damaged tissue an adhesive composition comprised of (i) a hydrophilic polymer; (ii) a crosslinkable component having several nucleophilic groups; and (iii) a crosslinkable component having several electrophilic groups capable of reaction with the nucleophilic groups to form covalent bonds, wherein crosslinkable components are biocompatible and nonimmunogenic, and at least one of components is hydrophilic polymer. Crosslinking of the composition is said to result in a biocompatible, nonimmunogenic, cross-linked matrix.

U.S. Pat. No. 7,868,123 entitled "Derivatized tertiary amines and uses thereof" teaches tertiary amine intermediate and electrophilic monomers derived therefrom. The invention also relates to adhesives or sealants derived from such electrophilic moieties.

Published U.S. Patent Application No. 2008/0220047 by Sawhney et al. and entitled "Low-swelling biocompatible hydrogels" teaches surgical treatment for treating a tissue inside a vertebral column by forming a low-swelling biodegradable hydrogel in situ that is adherent to a tissue inside the vertebral column. Sawhney teaches a method comprising: forming a low-swelling biodegradable hydrogel by in situ polymerization that is adherent to tissue inside a vertebral column and substantially exterior to the vertebral column, wherein the first functional groups comprise nucleophiles and the second functional groups comprise electrophiles, wherein the first synthetic precursor is selected from the group consisting of dilysines, trilysines, and tetralysines, wherein the second synthetic precursor comprises a multi-armed precursor possessing a core and arms, the arms each comprising a polyethylene glycol having a molecular weight from about 250 to about 5000, wherein the core is selected from the group consisting of polyethers, polyamino acids, proteins, and polyols, and wherein forming the hydrogel comprises reacting a first synthetic precursor comprising at least three of a first functional group with a second synthetic polymer precursor comprising at least three arms that each comprise a second functional group, wherein the first functional group reacts with the second functional group to form covalent crosslinks between the first synthetic precursor and the second synthetic polymer precursor, and wherein the hydrogel swells upon exposure to a physiological solution.

Published U.S. Patent Application No. 2007/0280988 by Ludwig et al. and entitled "Coating layers for medical devices and methods of making the same" teaches methods for controlling the morphology and the release-rate of active agent from coating layers for medical devices comprising a polymer matrix and one or more active agents. The methods comprise fixing the morphology or phase distribution of the active agent prior to removing solvent from the coating composition. The coating layers can be used for controlled delivery of an active agent or a combination of active agents.

Published U.S. Patent Application No. 2010/0173843 by Hnojewyj and entitled "Tissue Adhering Compositions" discloses a method which mixes a first component, a second component, and a buffer material. The first component includes an electrophilic polymer material comprising poly (ethylene glycol) having a functionality of at least three. The second component includes a nucleophilic material comprising a natural or synthetic protein at a concentration of about 25% or less that, when mixed with the first component within a reaction pH range, cross-links with the first component to form a non-liquid, three-dimensional barrier. The buffer material includes tris-hydroxymethylaminomethane having a pH within the reaction pH range. The method applies the mixture to adhere to a tissue region.

Published U.S. Patent Application No. 2010/0063459 A1 discloses an adhesive material for medical use comprising gelatin and a non-toxic cross-linking material, such as transglutaminase. An optional embodiment of the invention includes dressings in which a layer of a transglutaminase is sandwiched between a first and second layer of gelatin. The hemostatic products are useful for the treatment of wounded tissue.

U.S. Pat. No. 6,730,299 is directed to an adhesive protein foam for surgical and/or therapeutic uses discloses an adhesive matrix that is produced using a mixture of a protein compound in solution, preferably of the native collagen, of the heated collagen or of the albumin, with an oxidized polysaccharide or mucopolysaccharide, preferably oxidized starch, oxidized dextran or oxidized hyaluronic acid.

Published Patent Application No. WO1998/000161 A1 entitled "Fibrin-based systems for controlled release of medicinal" discloses a medicinal delivery system based on the enzyme-catalyzed conversion of fibrinogen to fibrin that forms a gel to entrap the medicinal. For certain protein medicinals, after adequate fibrinogen conversion but prior to gelation, a thrombin inhibitor is added along with the medicinal protein to protect the medicinal protein from fragmentation by the action of thrombin. The erosion rate of the matrix is altered by incorporation of fibrinolysis inhibitors, adjusting the concentration of matrix components, and including Factor XIII at various levels.

Published U.S. Patent Application No. 2009/0010982 A1 entitled "Biocompatible adherent sheet for tissue sealing" discloses a biocompatible adherent sheet for use in surgical and medical procedures for sealing the tissues of a living mammal, preferably a human. The biocompatible adherent sheet includes a carrier sheet including a biocompatible polymer and a modified chitosan evenly disposed on one or both surfaces of the carrier sheet. Methods of preparing a biocompatible adherent sheet and methods of using a biocompatible adherent sheet are also provided. The biocompatible adherent sheet may also include a bioactive agent and other active ingredients. The biocompatible adherent sheet is a soft, pliable material that adheres to various tissues, bends easily around curved surfaces, and can withstand moderate burst pressures. Further, the biocompatible adherent sheet described therein is said to provide better adhesion to body tissues than existing materials.

U.S. Pat. No. 6,132,759 entitled "Medicaments containing gelatin cross-linked with oxidized polysaccharides" discloses a wound dressing comprising a biopolymer matrix comprising gelatin cross-linked with an oxidized polysaccharide. Preferably said oxidized polysaccharide comprises an oxidized dextran or an oxidized xanthan. Preferably said matrix is in the form of a hydrated film, a hydrated or dry foam, dry fibers which may be fabricated into a woven or non-woven tissue, hydrated or dry microbeads, dry powder; or said matrix is covered with a semipermeable film, so as to control the humidity of the wound covered with the dressing, with the permeability chosen so as to maintain this humidity within a therapeutically optimal window. A polysulfated polysaccharide with a M.W. greater than 30,000 kDa is mechanically entrapped during the formation of said matrix.

Published U.S. Patent Application No. 2006/0078536 A1 entitled "Polysaccharide-based polymer tissue adhesive for medical use" discloses a kit comprising: a) a first aqueous solution comprising an oxidized polysaccharide containing aldehyde groups, having a molecular weight of about 1,000 to about 1,000,000 Daltons, said oxidized polysaccharide having an equivalent weight per aldehyde group of about 90 to about 1500 Daltons, said solution containing from about 5% to about 40% by weight of the oxidized polysaccharide; and b) a second aqueous solution comprising a water-dispersible, multi-arm polyether amine wherein at least three of the arms are terminated by a primary amine group, wherein the multi-arm polyether amine has a molecular weight of about 450 to about 200,000 Daltons, said solution containing from about 5% to about 70% by weight of the multi-arm polyether amine.

Published U.S. Patent Application No. 2005/0002893 A1 entitled "Composition consisting of a polymer containing amino groups and an aldehyde containing at least three aldehyde groups" discloses a composition of at least two biocompatible components that can be chemically cross-linked together, in particular for gluing biological tissue, comprising at least the following components: a) aqueous solution of at least one polymer having amino groups b) aqueous solution of at least one aldehyde having at least three aldehyde groups, where the composition is free of protein. The invention further relates to a provision of the composition for use as surgical tissue glue, and to a kit consisting of two substantially separate containers which contain components of the composition.

U.S. Pat. No. 6,096,309 entitled "Compositions containing thrombin and microfibrillar nanometer collagen, and methods for preparation and use thereof" discloses thrombin-containing hemostatic compositions, their preparation and use. In particular, the patent relates to hemostatic compositions comprising stabilized thrombin and microfibrillar collagen in an aqueous medium. The compositions are used in a kit comprising two different components, one of which is autologous patient's plasma as the source of fibrinogen, and the other of which is the thrombin-containing composition which also contains microfibrillar collagen having an average diameter of about 3-30 nanometers.

Other background references, include patent publications EP2,100,628 A1 "Self-degradable adhesive for medical use of two-component reactant system comprising powder-liquid or powder-powder"; published PCT application WO2008/005207 A2 entitled "Tissue adhesives with modified elasticity"; published US Patent Application No. 2008/0319101 A1 entitled "Medical-use two part reactive adhesive and medical-use resin having self-degradation property"; published US Patent Application No. 2008/0213243 A1 entitled "Hemostatic materials and dressing"; published US Patent Application No. 2008/0075657 A1 entitled "Biopolymer system for tissue sealing"; and published US Patent Application No. 2003/0232746 A1 entitled "Cross-linked bioactive hydrogel matrices".

Additional related background references include publications: Catheterization and Cardiovascular Diagnosis 41:79-84 (1997) that discloses collagen as a reinforcement matrix in fibrin sealant; "Fibrin: A versatile Scaffold for Tissue Engineering Applications", Tissue Engineering: Part B Volume 14, Number 2, 2008, pgs. 199-215; and "Cross-linking of human fibrinogen with glutaraldehyde and tetranitromethane", Thrombosis research (1975), 7, 827-38.

SUMMARY OF THE INVENTION

Figure 1:
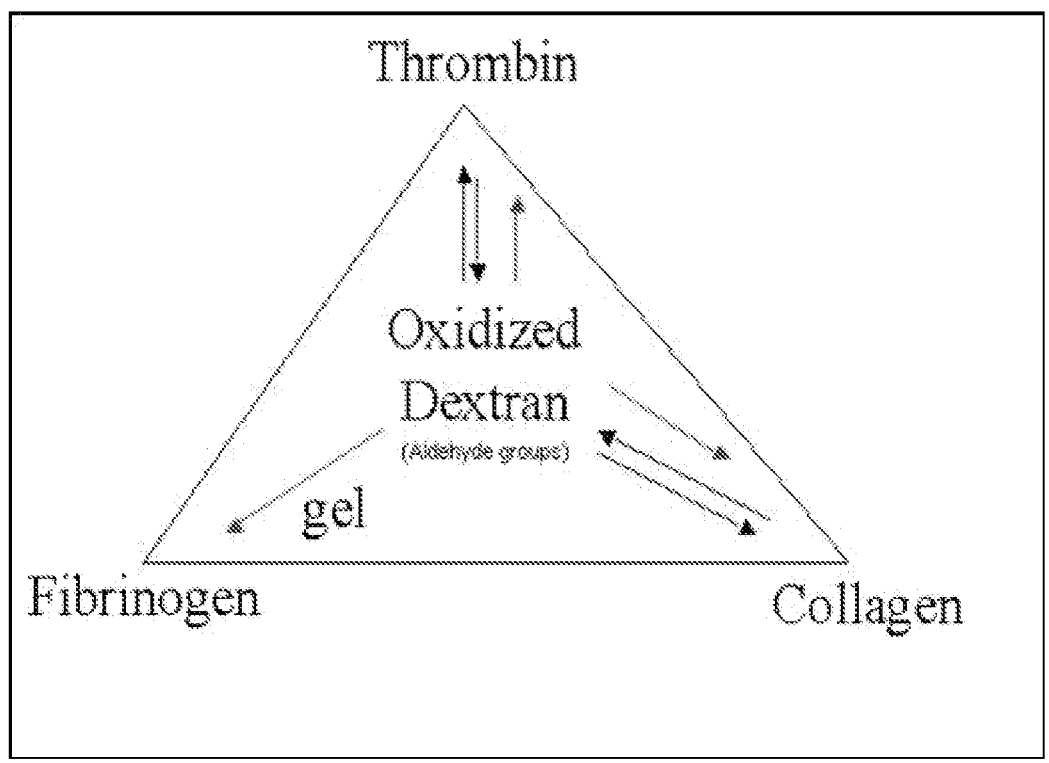
FIG. 1 shows schematic diagram of crosslinking mechanism of the present invention

According to an embodiment of the present invention, a tissue sealant, adhesive, hemostat, or scaffolding material comprises: thrombin, fibrinogen, a biocompatible particulate material having amine functionality, said biocompatible particulate material is selected from the group consisting of gelatin, hyaluronic acid, chondroitin-6-sulfate, collagen, and chitosan; and a biocompatible polymer containing aldehyde groups, wherein said biocompatible polymer is oxidized dextran or polyvinyl alcohol acetoacetate.

In one embodiment, the tissue sealant, adhesive, hemostat, or scaffolding material further comprises water. In one embodiment, the biocompatible particulate material is atelocollagen, and the biocompatible polymer containing aldehyde groups is oxidized dextran. In one embodiment, the tissue sealant, adhesive, hemostat, or scaffolding material is a two-part system comprising a first solution and a second solution, wherein said first solution comprises thrombin, atelocollagen, and oxidized dextran and wherein said second solution comprises fibrinogen and DABCO.

In one embodiment, the concentration of atelocollagen is about 2%; and particle size of atelocollagen is less than 100 micron; and concentration of oxidized dextran is about 10% by volume.

In one embodiment, the first solution and the second solution are sprayed substantially simultaneously or sequentially on the tissue to form sealant, adhesive, hemostat, or scaffolding.

According to an embodiment of the present invention, a method of forming tissue sealant, adhesive, hemostat, or scaffolding material comprises the step of forming on the tissue surface a mixture of thrombin, fibrinogen, a biocompatible particulate material having amine functionality, said biocompatible particulate material selected from the group consisting of gelatin, hyaluronic acid, chondroitin-6-sulfate, collagen, and chitosan; and a biocompatible polymer containing aldehyde groups, wherein said biocompatible polymer is oxidized dextran or polyvinyl alcohol acetoacetate.

DETAILED DESCRIPTION OF THE INVENTION

According to an embodiment of the present invention, the addition of collagen or gelatin particulates along with crosslinking improves the strength of the fibrin sealant-based compositions. While crosslinking with thrombin might be expected to reduce the level of thrombin available to react with fibrinogen, the inventor discovered a process for crosslinking collagen or gelatin particles (typically having size less than 500 microns, more preferably less than 100 microns) into a fibrin hydrogel that does not compromise the level of thrombin biologic activity. The process provides for crosslinking of a fibrin-based sealant composition with collagen and an aldehyde-containing polymer. Crosslinking a fibrin-based sealant into a hydrogel with a polymer having aldehyde groups surprisingly does not significantly diminish the biologic activity of thrombin and enables the formation of a better biologic based sealant having increased strength.

The fibrinogen component of the fibrin sealant is preferably derived from a cryoprecipitate that was concentrated by ultra filtration for example as described in WO94/022503. The fibrinogen component preferably comprises a fibrinogen content of from about 15-150 mg/ml, in particular from 20-80 mg/ml. The amount of fibrinogen can be measured according to a number of methods known to these skilled in the art, such as, for instance, Clauss' method or any other appropriate fibrinogen assay method, as reviewed for example in Mackie et al., "Guidelines on fibrinogen assays", British Journal of Haematology, 2003, 121, 396-404.

Fibrin sealants function as hemostatic agents in a manner that are analogous to the natural blood clotting cascade. Fibrin sealants are generally derived from two components prior to the application in surgical operations.

One component, as described above, contains fibrinogen which upon exposure to a proteolytic enzyme such as human thrombin forms fibrin which is the polymer forming the basic material of the natural blood clot. During surgical operations the two components are applied, for example, by two syringes which are emptied simultaneously by mixing the two components as fast as possible and avoiding the blockage of the supply lines.

Therefore, the subject of the present invention is also a two component fibrin sealant comprising separately components A and B wherein component A comprises a fibrinogen solution and a component B comprising a solution of a proteolytic enzyme that is capable to react with fibrinogen to form fibrin. The fibrinogen solution preferably includes a catalyst, such as 1,4-diazabicyclo[2.2.2]octane (DABCO).

Preferably, the proteolytic enzyme is human thrombin in particular having an activity of from about 2 to 4,000 IU/ml. The activity of thrombin is measured according to the clotting assay (European Pharmacopoeia). It is understood by the skilled person that fibrin glue may be defined by its content of clottable protein instead of the definition based on clottable fibrinogen.

Collagen is a common protein that makes up a significant part of the living body, whether human or animal. As a structural protein, collagen is essential to creating the body's physical structure, and as an extracellular matrix it acts as a supporting framework over which our cells are arranged. The collagen molecule is composed of three intertwined peptide chains. It is a rigid protein 300 nm in length, 1.5 nm in diameter, and approximately 300 kilodaltons (kDa) in molecular weight.

Collagen sources are well-known and may include, bovine collagen, such as Type 1 bovine collagen, as well as porcine collagen, porcine small intestine submucosa, and fetal bovine skin. Atelocollagen is a collagen solubilized by protease, but its physical properties are virtually identical to those of natural, unsolubilized collagen. Porcine collagen is commonly used as an active ingredient of the adhesive/hemostatic agents. In order to be used, porcine collagen is rendered non-immunogenic by removing telopeptides therefrom to produce atelocollagen.

Collagen is known for its very low antigenicity (or reactivity, i.e., it causes little immune response) because most of the collagen molecule is composed of a G-X-Y amino acid sequence that differs little even among different animal species. The slight amount of antigenicity that is seen in collagen is thought to be due to the telopeptides attached to each end of the collagen molecule, which do not contain the G-X-Y sequence. Since the telopeptides are not present in atelocollagen, the antigenicity of atelocollagen is even lower than that of collagen.

The present invention relates to the unexpected finding that polymers comprising collagen or gelatin that has been cross-linked with oxidized polysaccharides in a fibrin sealant composition constitute excellent medicament such as dressings for the treatment of wounds. The cross links are formed by Schiff base formation between free amino groups of the collagen/gelatin and aldehyde groups in the polysaccharides. A polysaccharide that is particularly suited for use in the present invention is dextran, more preferably an oxidized dextran or xanthan.

The oxidized polysaccharides used in the present invention are preferably an oxidized dextran in solution. However, it shall be obvious to the person skilled in the art that other polysaccharides with suitable viscosity, molecular mass and oxidation properties can also be used, as described in the above-mentioned patent application EP 308,330 by Schacht and Nobels, the contents of which are hereby incorporated by reference.

The molecular weight of the oxidized dextran used for the fabrication of wound dressings according to the invention is preferably below 5,000,000, more preferably between 10,000 and 100,000, in such a way that the viscosity of the aqueous solution of the dextran is not too high, for example between 0.1 and 1 Pa·s for a 2% solution (as measured using a Brookfield LVT viscosimeter operated at 30 cycles).

Oxidation of dextran is a well-known reaction. For instance, oxidation can be conveniently obtained by treatment with an aqueous solution of a salt of periodic acid, such as sodium periodate. The purpose of the oxidation is to create the formation of reactive dialdehyde residues in the polysaccharides. Although the oxidation procedure described above is preferred, it shall be clear to the person skilled in the art that other oxidation methods leading to the formation of dialdehyde residues are also possible, for instance, by treatment with periodic acid or lead tetra acetate in an organic solvent such as dimethylsulfoxide. After oxidation, the oxidized dextran can be conveniently purified and separated from low molecular weight reaction components by classical purification methods. Examples to accomplish this include, but are not limited to: precipitation (for instance by addition of acetone, methanol or isopropanol) or dialysis, ultrafiltration or gel permeation chromatography, followed by lyophilisation.

Cross-linking between collagen or gelatin and oxidized dextran is accomplished in-situ by the formation of so-called Schiff base links between free amino groups present on the collagen/gelatin (notably on the lysine residues thereof) and the dialdehyde residues on the oxidized dextran and the fibrinogen. This reaction is performed in an aqueous fibrin sealant medium and the speed and degree of cross-linking are dependent on a variety of parameters, such as the type of collagen/gelatin, the concentration, degree of dialdehyde substitution and molecular weight of the oxidized dextran, the pH, buffer type and the presence of electrolytes in the reaction medium, etc. Suitable reaction parameters are described for instance in patent application published European Patent Application 308330. For the purpose of this invention, the percentage of oxidation of the oxidized dextran is preferably between 5% and 50%. The concentrations of collagen/gelatin and oxidized dextran are preferably between about 2% and about 20%, more preferably between 5 and 15%, even more preferably between 7 and 12%.

Referring to now to FIG. 1, a schematic diagram illustrates the crosslinking mechanism of the present invention. Amine groups (e.g., those available from collagen and thrombin) react with aldehyde groups on the polymer to form a Schiff base by elimination of water. The formation of Schiff base depends on amount of water and number of functional groups. In large amount of water, the equilibrium will favor dissociated state. In the figure double arrows show reversible state of the Schiff base chemistry that favor dissociated state in the presence of water.

The collagen is believed to act as filler and reinforcement matrix that crosslinks with other collagen chains along with fibrin through the dialdehyde groups on the oxidized dextran. When thrombin sets up crosslinking of fibrin through biological cascade and forms a stable gel, the chemical crosslinking through oxidized dextran takes place that is shown with single arrows in FIG. 1.

This novel approach of crosslinking clearly shows its benefit by making fibrin glue stronger. Increasing crosslinking of fibrin glue should also slow the rate of degradation. Having additional crosslinks in the inventive composition may also slow down degradation of modified fibrin sealant. Other reinforcing materials with amine functionality can be utilized, including chitosan. Alternatively, water soluble polymers such as hyaluronic acid, gelatin, etc. can be utilized as reinforcing component. Besides oxidized dextran that has aldehyde groups for crosslinking, one can also use other water stable crosslinking reagents for e.g. polyvinyl alcohol acetoacetate and xanthan.

In another embodiment of the present invention, latent chemical crosslinking through chemical crosslinking agent where chemical crosslinking reagent can be coated with water soluble polymer such as biocompatible polyesters or other polymers that would not interfere with biological clotting mechanism and becomes active when the coated layer dissolves away setting up delayed crosslinking A variety of chemical crosslinking agents can be used that may be susceptible to hydrolysis, such as NHS ester derivatives of PEG or other moieties with NHS ester groups.

The inventive liquid fibrin sealant composition is a multi-component system that comprises component A containing a solution of fibrinogen as described above and component B containing a protolytic enzyme as described above, preferably thrombin, and an aldehyde-containing polymer, such as oxidized dextran or xanthan. A catalyst, such as 1,4-diazabicyclo[2.2.2]octane, is preferably provided in component A, the fibrinogen component. The inventive liquid fibrin sealant composition can be applied onto a tissue surface by drip or spray from a conventional device in which the components are caused to combine either on the surface or within the device prior to dispensing. A preferred delivery device is a dual syringe device having a multi-lumen dispensing tube in which the two components are dispensed from the device separately into an air stream that atomizes and disperses the components. The components react upon contact, gel and form the desired fibrin-based scab on the tissue surface.

Additional details with regard to the inventive compositions and process are provided in the following non-limiting examples.

EXAMPLE 1

A 10% by volume aqueous solution of bovine fibrinogen crosslinks in less than 1 minute when combined with 10% v/v solution of oxidized dextran (5% w/w in water) in presence of DABCO as a catalyst. Evicel® fibrin sealant (Distributed by Ethicon, Inc., Somerville, N.J. and manufactured by Omrix Biopharmaceuticals Ltd., Israel) is a two-part liquid sealant consisting of fibrinogen component (55-85 mg/mL fibrinogen) and a thrombin component (800-1200 IU/mL human thrombin). Evicel fibrin sealant is generally provided as a single use kit consisting of two packages: One package contains one vial of so-called Biological Active Component 2 (BAC2) and one vial of thrombin. BAC2 is a sterile solution having a pH of between 6.7-7.2 and consists primarily of a concentrate of human fibrinogen. The BAC2 component contains a concentrate of human fibrinogen (55-85 arginine hydrochloride, glycine, sodium chloride, sodium citrate, calcium chloride and water for injection (WFI) is available. The thrombin component is a sterile solution having a pH of between 6.8-7.2 that contains purified human thrombin. The thrombin component in solution contains human thrombin (800-1200 IU/ml), calcium chloride, human albumin, mannitol, sodium acetate and water for injection (WFI).

EXAMPLE 2

A ten percent (10%) by volume solution of oxidized dextran is combined with the thrombin component of Evicel kit described above, while DABCO is added to the fibrinogen component in a first experimental set. The two solutions are dispensed at a one to one volumetric ratio and caused to mix on a test surface using a conventional dual syringe spray device. The resulting mixture immediately gels indicating that thrombin has not been deactivated as a result of the addition of oxidized dextran.

EXAMPLE 3

One hundred (100) milligrams of atelocollagen is added to a five (5) mL of thrombin solution that also contains a ten percent (10%) by volume solution of oxidized dextran as described above. The solution is left to stand for 30 minutes to see any changes. No gel forms. This modified thrombin solution is sprayed along with a fibrinogen solution as described above with DABCO in an ex-vivo GI (gastrointestinal) study to measure burst pressure.

Figure 2:
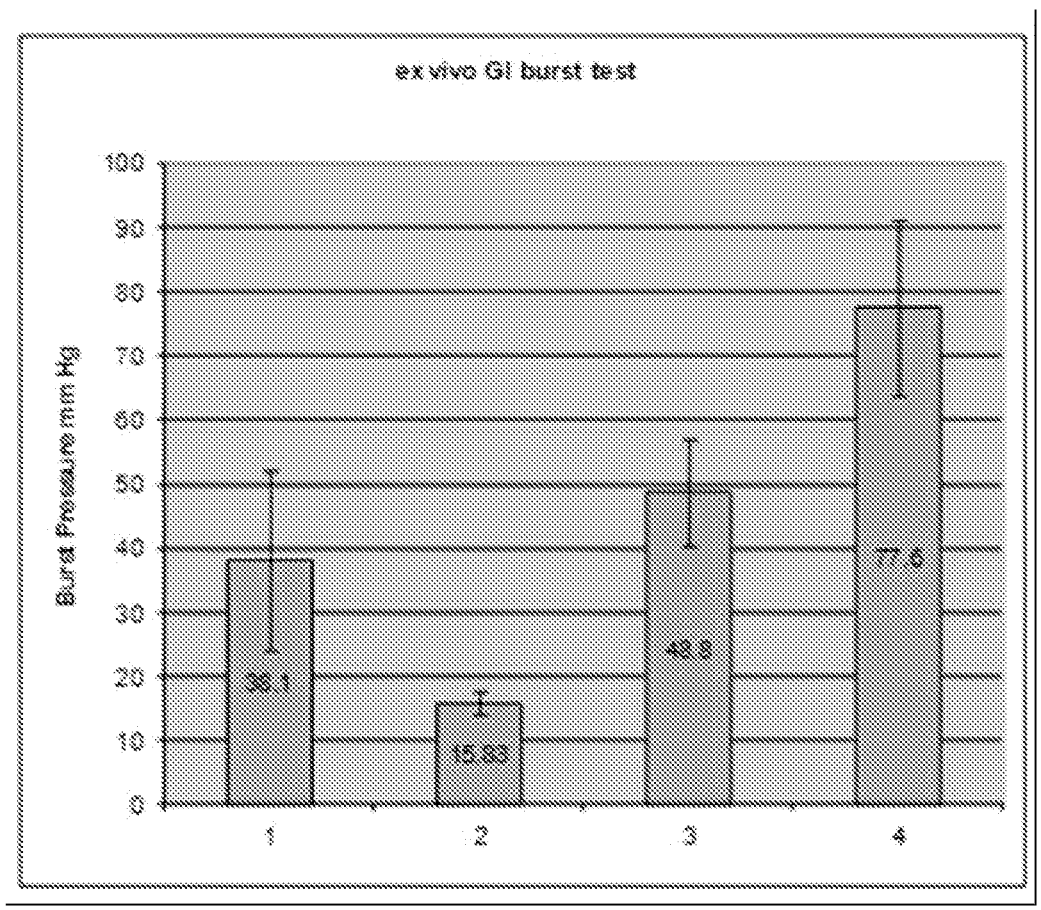
FIG. 2 shows the results of the Ex Vivo GI (gastrointestinal) Burst Test

Results are compared in reference to FIG. 2 with sprayed solutions of the Evicel fibrin sealant alone, Evicel fibrin sealant with only collagen, and Evicel fibrin sealant with both collagen and oxidized dextran. Point 1 corresponds to Evicel fibrin sealant alone; Point 2 corresponds to Evicel fibrin sealant and oxidized dextran; Point 3 corresponds to Evicel fibrin sealant and 2.5% by weight of atelocollagen; Point 4 corresponds to Evicel fibrin sealant and 2% by weight or volume of atelocollagen and 10% by volume of oxidized dextran.

FIG. 2 indicates that the Evicel fibrin sealant alone has an average burst pressure of 38 mm Hg. Evicel fibrin sealant with 2.5% by weight atelocollagen has an average burst pressure of 49 mm Hg. Evicel fibrin sealant with oxidized dextran, DABCO catalyst and 2% wt atelocollagen has an average burst pressure of 78 mm Hg. These results suggest the formation of a crosslinked structure between the oxidized dextran, fibrinogen and collagen with burst strength that is superior to fibrin sealant alone or in combination collagen.

Although this invention has been shown and described with respect to detailed embodiments thereof, it will be understood by those skilled in the art that various changes in form and detail thereof may be made without departing from the spirit and scope of the claimed invention.

I claim:

1. A tissue sealant, adhesive, hemostat, or scaffolding material, wherein said tissue sealant, adhesive, hemostat, or scaffolding material is a two-part system comprising a first solution and a second solution, comprising:
   thrombin, fibrinogen, a biocompatible particulate material having amine functionality, said biocompatible particulate material is atelocollagen
   a biocompatible polymer containing aldehyde groups, wherein said biocompatible polymer is oxidized dextran or polyvinyl alcohol acetoacetate; and a catalyst,
   wherein said first solution comprises thrombin, biocompatible particulate material, and the biocompatible polymer;
   wherein said second solution comprises fibrinogen and the catalyst; and wherein said catalyst is DABCO.

2. The tissue sealant, adhesive, hemostat, or scaffolding material of claim 1, wherein the biocompatible polymer containing aldehyde groups is oxidized dextran.

3. The tissue sealant, adhesive, hemostat, or scaffolding material of claim 2,
   wherein the biocompatible particulate material is atelocollagen, and
   wherein the biocompatible polymer containing aldehyde groups is oxidized dextran.

4. The tissue sealant, adhesive, hemostat, or scaffolding material of claim 3,
   wherein said first solution comprises thrombin, atelocollagen, and oxidized dextran and
   wherein said second solution comprises fibrinogen and DABCO.

5. The tissue sealant, adhesive, hemostat, or scaffolding material of claim 4,
   wherein concentration of atelocollagen is about 2%;
   particle size of atelocollagen is less than 100 micron;
   concentration of oxidized dextran is about 10% by volume,
   and the molecular weight of oxidized dextran is between about 10,000 and 100,000.

6. The tissue sealant, adhesive, hemostat, or scaffolding material of claim 5, wherein said first solution and said second solution are sprayed substantially simultaneously or sequentially on the tissue to form sealant, adhesive, hemostat, or scaffolding.

* * * * *